United States Patent
Claeys

(10) Patent No.: US 11,198,885 B1
(45) Date of Patent: Dec. 14, 2021

(54) GENETIC REGULATORY ELEMENT

(71) Applicant: Inari Agriculture Technology, Inc., Cambridge, MA (US)

(72) Inventor: Hannes Bart Claeys, Ghent (BE)

(73) Assignee: Inari Agriculture Technology, Inc., Cambridge, MA (US)

( * ) Notice: Subject to any disclaimer, the term of this patent is extended or adjusted under 35 U.S.C. 154(b) by 0 days.

(21) Appl. No.: 17/249,437

(22) Filed: Mar. 2, 2021

Related U.S. Application Data

(60) Provisional application No. 63/084,150, filed on Sep. 28, 2020.

(51) Int. Cl.
*C12N 15/82* (2006.01)

(52) U.S. Cl.
CPC ................ *C12N 15/8216* (2013.01)

(58) Field of Classification Search
None
See application file for complete search history.

(56) References Cited

U.S. PATENT DOCUMENTS

| | | | |
|---|---|---|---|
| 2003/0049814 A1* | 3/2003 | Andrews | C12N 9/1092 435/183 |
| 2015/0059010 A1 | 2/2015 | Cigan et al. | |
| 2015/0082478 A1 | 3/2015 | Cigan et al. | |

FOREIGN PATENT DOCUMENTS

| | | |
|---|---|---|
| WO | 2018140899 A1 | 8/2018 |
| WO | 2018183878 A1 | 10/2018 |

OTHER PUBLICATIONS

Wilson, et al. "The lactose repressor system: paradigms for regulation, allosteric behavior and protein folding". Cell Mol Life Sci. 64: 3-16. (Year: 2007).*

(Continued)

*Primary Examiner* — Ashley K Buran
*Assistant Examiner* — David R Byrnes
(74) *Attorney, Agent, or Firm* — McKee, Voorhees & Sease, PLC

(57) ABSTRACT

An expression increasing element comprising a 36 nucleotide DNA sequence that can be used to increase the expression of genes, and in particular to increase the expression of endogenous plant genes, in plants is disclosed. Also disclosed are plants, plant parts, and commodity plant products comprising the expression increasing element along with related methods of using the expression increasing element and plants comprising the expression increasing element.

30 Claims, 5 Drawing Sheets

Specification includes a Sequence Listing.

(56) References Cited

OTHER PUBLICATIONS

Davey and Wilson. "Deconstruction of complex protein signaling switches: a roadmap toward engineering higher-order gene regulators". Nanomed Nanobiotechnol. 9: 1-15. (Year: 2017).*
Fiering et al. "Single cell assay of .a transcription factor reveals a threshold m transcription activated by signals emanating from the T-cell antigen receptor". Genes Dev. 4: 1823-1834. (Year: 1990).*
Bortesi, Luisa, et al., "The CRISPR/Cas9 system for plant genome editing and beyond", Biotechnology Advances, vol. 33, pp. 41-52, 2015.
Ellis, J.G., et al., "The ocs element: a 16 base pair palindrome essential for activity of the octopine synthase enhancer", The EMBO Journal, vol. 6, No. 11, pp. 3203-3208, 1987.
Ellis, Jeffrey G., et al., "Does the ocs-element occur as a functional component of the promoters of plant genes?", The Plant Journal, vol. 4, No. 3, pp. 433-443, 1993.
Singh, Karambir, et al., "Saturalion mutagenesis of the octopine synthase enhancer: Correlation of mutant phenotypes with binding of a nuclear protein factor", Proc. Natl. Acad. Sci. USA, vol. 86, pp. 3733-3737, May 1989.

* cited by examiner

US 11,198,885 B1

GENETIC REGULATORY ELEMENT

REFERENCE TO SEQUENCE LISTING SUBMITTED ELECTRONICALLY

The sequence listing contained in the file named "10074US1_ST25.txt", which is 12,909 bytes as measured in the Windows operating system, and which was created on Feb. 25, 2021 and electronically filed via EFS-Web on Mar. 2, 2021, is incorporated herein by reference in its entirety.

BACKGROUND

Methods of using CRISPR, Zinc Finger Nuclease, and Transcription activator like effector Nuclease (TALEN) technology for genome editing in plants are disclosed in US 20150082478, US 2015/0059010A1, and Bortesi et al., 2015, Biotechnology Advances, pp. 41-52, Vol. 33, No. 1. Ellis et al., 1987, EMBO J. (6):11:3203-3208, disclose a 16 base pair bacterial octopine synthase gene enhancer element that could increase expression of exogenous genes in maize and tobacco protoplasts in transient expression assays. PCT Patent Application WO 2018/140899 discloses insertion of expression-enhancing elements with homology to the bacterial octopine synthase gene enhancer element in the promoter region of a maize Lc gene in a maize protoplast genome to increase expression of that gene. There is an ongoing need for plant-derived sequences capable of reliably increasing transcription of plant genes.

SUMMARY

DNA molecules comprising the polynucleotide sequence of SEQ ID NO:3 are provided. Also provided are biological samples, plant chromosomes, plant cells, tissue cultures of regenerable cells comprising the plant cells, plant parts, and plants comprising the polynucleotide sequence of SEQ ID NO:3. In certain aforementioned embodiments, the polynucleotide sequence of SEQ ID NO:3 is operably linked to a polynucleotide sequence comprising a promoter, wherein the promoter is optionally an endogenous promoter, and wherein the endogenous promoter is optionally located in a plant chromosome. Also provided is the use of the aforementioned DNA molecules comprising the polynucleotide sequence of SEQ ID NO:3 to: (i) increase expression of one or more elements encoded by a transcription unit which is operably linked to the promoter in a plant; (ii) confer a useful trait to a plant comprising the recombinant DNA molecule, wherein the useful trait is optionally improved abiotic stress, architecture, biotic stress tolerance, photosynthesis, or resource partitioning relative to a control plant lacking the recombinant DNA molecule; (iii) obtain a plant or seed therefrom exhibiting the useful trait of (ii); or (iv) to grow a population of plants exhibiting the useful trait of (ii); optionally wherein the plant of (i), (ii), (iii), or (iv) is a maize, soybean, cotton, or canola plant; or optionally wherein the seed of (iii) is a maize, soybean, cotton, or canola plant.

Methods of plant seed production comprising crossing plants comprising the aforementioned DNA molecules comprising the polynucleotide sequence of SEQ ID NO:3 with a second plant to produce plant seed and optionally harvesting the seed are provided.

Methods of plant seed production comprising selfing plants comprising the aforementioned DNA molecules comprising the polynucleotide sequence of SEQ ID NO:3 to produce plant seed and optionally harvesting the seed are provided.

Methods of producing a plant comprising an added desired trait comprising introducing a transgene, a targeted genetic change, or genetic locus conferring the desired trait into plants comprising the aforementioned DNA molecules comprising the polynucleotide sequence of SEQ ID NO:3 are provided.

Methods of producing a commodity plant product comprising processing a plant or seed comprising the aforementioned DNA molecules comprising the polynucleotide sequence of SEQ ID NO:3 and recovering the commodity plant product from the processed plant or seed are provided.

Methods of producing plant material, the method comprising growing a plant having an expression increasing element comprising SEQ ID NO:3 operably linked to a transcript-encoding polynucleotide, wherein the expression of the transcript-encoding polynucleotide in said plant is increased when compared to a control plant lacking the expression increasing element are provided.

Methods of producing plant material comprising: (a) providing a plant having an expression increasing element comprising SEQ ID NO:3 operably linked to a transcript-encoding polynucleotide, wherein the expression of the transcript-encoding polynucleotide is increased in said plant when compared to a control plant lacking the expression increasing element; and (b) growing the plant under conditions that allow for expression of the transcript promoting polynucleotide are provided.

Methods of identifying biological samples comprising a polynucleotide comprising a modified plant gene comprising the step of detecting the presence of SEQ ID NO:3 in the biological sample are provided.

Methods of producing a treated plant seed comprising contacting a seed comprising the aforementioned DNA molecules comprising the polynucleotide sequence of SEQ ID NO:3 with a composition comprising a biological agent, insecticide, or fungicide are provided.

Methods of increasing the expression of an RNA molecule in a plant comprising expressing an RNA molecule encoded by a DNA molecule in the plant, wherein the DNA molecule encoding the RNA molecule is operably linked to one or more DNA molecules comprising: (i) an expression increasing element comprising SEQ ID NO:3; (ii) a promoter; and optionally (iii) DNA molecules encoding a 5' untranslated region (5' UTR), an intron, an exon, a 3' UTR, a polyadenylation site, or combination thereof; wherein the expression of the RNA is increased in comparison to a control plant lacking the expression increasing element are provided.

BRIEF DESCRIPTION OF THE DRAWINGS/FIGURES

DETAILED DESCRIPTION

Figure 1:
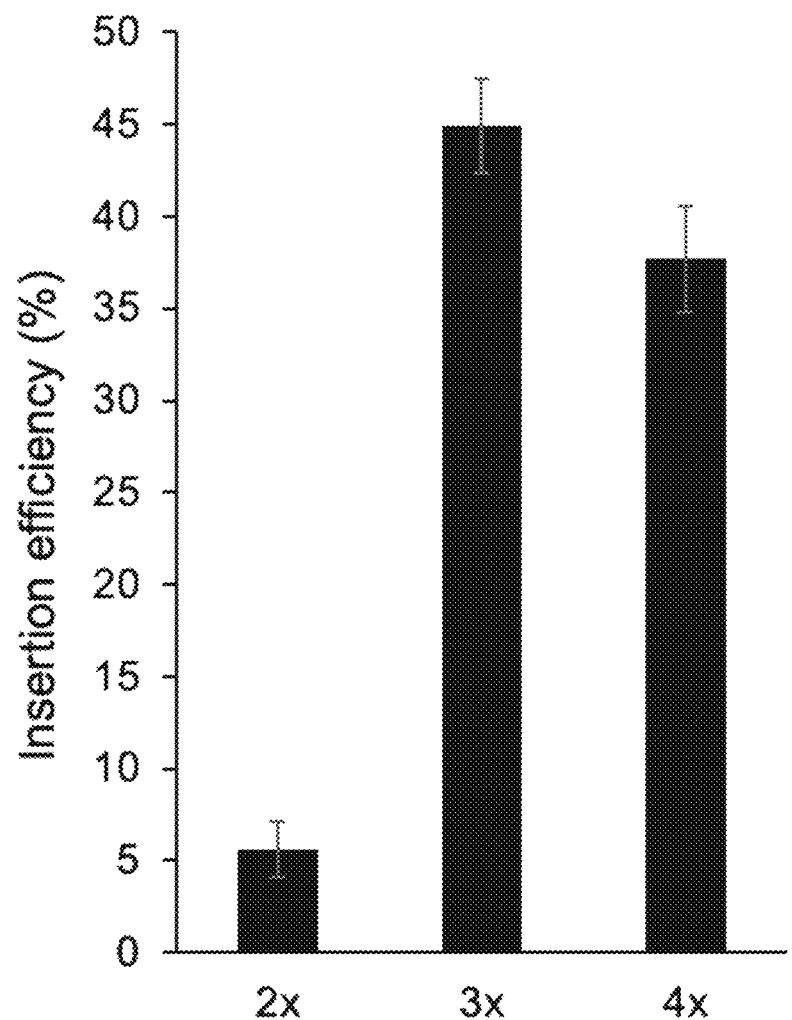
FIG. 1 depicts insertion efficiency of a dimer (SEQ ID NO:2), trimer (SEQ ID NO:3), or tetramer (SEQ ID NO:4) of the 12 nucleotide core element (SEQ ID NO:1) inserted into the ZmGln1-3 promoter.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part).

As used herein, the phrases "endogenous promoter," "endogenous gene," "endogenous plant transcription unit" and the like refer to the native form of a promoter, gene, or plant transcription unit in its natural location in the organism or in the genome of an organism.

The term "exogenous" as used herein with regards to a DNA molecule, nucleotides, or polynucleotides inserted into a plant genome refer to any DNA molecule, nucleotide, or polynucleotide that is synthetic or that has been removed from its native location and that has been inserted into a new genomic location.

The term "isolated" as used herein means having been removed from its natural environment.

As used herein, the terms "include," "includes," and "including" are to be construed as at least having the features to which they refer while not excluding any additional unspecified features.

As used herein, the phrase "operably linked" refers to a juxtaposition wherein the components so described are in a relationship permitting them to function in their intended manner. For instance, a promoter is operably linked to a coding sequence if the promoter affects its transcription or expression. In another non-limiting example, an "expression increasing element" (e.g., a transcriptional enhancer element) is operably linked to a promoter if the expression increasing element increases activity of the promoter (e.g., as measured by promoter-driven accumulation of a transcript or protein encoded a transcript).

As used herein, the terms "orthologous" or "orthologue" are used to describe genes or proteins encoded by those genes that are from different species but which have the same function (e.g., encode enzymes that catalyze the same reactions or encode transcriptional regulators that control expression of genes with similar functions). Orthologous genes will typically encode proteins with some degree of sequence identity (e.g., at least 40%, 50%, 60%, 70%, 80%, 90%, or 95% sequence identity, conservation of sequence motifs, and/or conservation of structural features).

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified DNA molecule" is used herein to describe a nucleic acid sequence which has been separated from other compounds including, but not limited to polypeptides, lipids and carbohydrates.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

An expression-increasing DNA element which can be used to increase expression of transcript-encoding polynucleotides in plants comprising the polynucleotide 5'-GTAAGCGCTTACGTAAGCGCTTACGTAAGCGCTTAC-3' (SEQ ID NO:3) is disclosed. Also disclosed are plants, plant parts (e.g., seeds, leaves, roots, stems), and regenerable or non-regenerable plant cells comprising SEQ ID NO:3. Biological samples including seed meal that comprise polynucleotides comprising SEQ ID NO:3 are also disclosed. Related methods of using plants, plant parts, and plant cells comprising SEQ ID NO:3 to produce plant materials including seeds or to produce plant commodity products comprising SEQ ID NO:3 are also disclosed.

Expression of endogenous plant genes can be increased by insertion or formation of SEQ ID NO:3 in an endogenous plant gene such that SEQ ID NO:3 is operably linked to the endogenous promoter of the plant gene. In certain embodiments, operable linkage to the endogenous promoter is achieved by insertion or formation of one or more copies of SEQ ID NO:3 in one or more of an endogenous promoter, 5' untranslated region (5'UTR), intron, and/or 3' untranslated region of an endogenous plant gene. Since SEQ ID NO:3 comprises a palindrome, insertion or formation of the expression-increasing element in the endogenous gene is orientation independent. SEQ ID NO:3 comprises a triplication of the core element 12 nucleotide palindromic repeat unit GTAAGCGCTTAC (SEQ ID NO:1).

The 12 core element nucleotide sequence of SEQ ID NO:1 is present at several locations in the corn genome. For example, it can be found at several chromosomal locations of the maize variety B73. According to the B73v4 version of the maize genomic sequences (available on the https world wide web internet site maizegdb.org/genome/assembly/Zm-B73-REFERENCE-GRAMENE-4.0 and hereinafter referred to as "B73v4 maize genome"), SEQ ID NO:1 can be found on Chr3 coordinates 1,063,395 . . . 1,063,406 (intron of Zm00001d039287), on Chr3 coordinates 12,253, 969 . . . 12,253,980 (immediately downstream of Zm00001d039695), on Chr3 coordinates 12,265,615 . . . 12,265,626 (intron of Zm00001d039695), on Chr3 coordinates 12,277,428 . . . 12,277,439 (intron of Zm00001d039695), on Chr3 coordinates 147,698,750 . . . 147,698,761 (not within 2 kb of an annotated gene model), on Chr6, coordinates 107,132,183 . . . 107,132,194 (about 2 kb downstream of Zm00001d036949), on Chr10, coordinates 53,761,662 . . . 53,761,673 (not within 2 kb of an annotated gene model). Since SEQ ID NO: 1 is palindromic it is also found on the complementary strand of those coordinates.

The 12 nucleotide core element nucleotide sequence of SEQ ID NO:1 is also present at several locations in the soybean genome. For example, it can be found at several chromosomal locations of the soybean variety W82 (Williams 82). According to the version of the soybean genomic sequences (available on the https world wide web internet site ncbi.nlm.nih.gov/genome entry "Glycine_max_v2.1" and hereinafter referred to as "W82 soybean genome"), SEQ ID NO:1 can be found on Chromosome 1 coordinates 44968347 to 44968358, on Chromosome 3 coordinates 3983755 to 398873766, on Chromosome 6 coordinates 26074553 to 26074564, and on Chromosome 19 coordinates 44574051 to 44574062, 44575338 to 44575349 (overlapping the GLYMA_19G187100 gene), and 44581677 to 44581688. Since SEQ ID NO: 1 is palindromic it is also found on the complementary strand of those coordinates.

In certain embodiments, a polynucleotide, plant gene, or plant comprising SEQ ID NO:3 can further comprise at least 1, 2, 3, or more additional copies of SEQ ID NO:1. Endogenous plant genes that are targeted for insertion or formation of SEQ ID NO:3 can comprise a promoter which is recognized by RNA polymerase II and is operably linked to a transcription unit. In certain embodiments, such transcription units can comprise transcription unit elements including a 5' untranslated region (5' UTR), an intron, an exon, a microRNA coding region, a microRNA precursor coding region, a 3' UTR, a polyadenylation site, or a combination thereof. In certain embodiments, the polynucleotide sequence of SEQ ID NO:3 is inserted or formed about 10, 20, 30, or 40 base pairs (bp) to about 100, 240, 300, 400, 500, 1000, 2000, 3000, or 5000 bp from the transcriptional start site (TSS) the transcription unit (i.e., the 5' cap site of the transcript produced by the transcription unit). In certain embodiments, the polynucleotide sequence of SEQ ID NO:3 is inserted or formed about 40 base pairs (bp) to about 100, 240, 300, or 400 bp from the transcriptional start site (TSS) the transcription unit. Insertion or formation of SEQ ID NO:3 can occur either 5' (i.e., upstream) or 3' (i.e., downstream) to the TSS of the transcription unit. In certain embodiments, insertion or formation of SEQ ID NO:3 is in the promoter of the endogenous gene (e.g., about 40 base pairs (bp) to about 100, 240, 300, or 400 bp 5' (i.e., upstream) of the TSS). Expression of a transgene that is integrated into the plant genome can also be increased by insertion or formation of SEQ ID NO:3 in the transgene such that it is operably linked to the promoter that is operably linked to the transgene. Expression of a transgene can also be increased by in vitro insertion or formation of SEQ ID NO:3 in the transgene such that it is operably linked to the promoter that is operably linked to transgene and then introducing the transgene into the plant genome (e.g., by *Agrobacterium*-mediated transformation or biolistics).

Expression of transcript-encoding polynucleotides which are operably linked to an increasing element comprising SEQ ID NO:3 can be increased in comparison to a control plant comprising the transcript-encoding polynucleotides but lacking the expression increasing element. Such increases in expression that are mediated by SEQ ID NO:3 can be measured by a variety of methods. In certain embodiments, a trait conferred by increased expression the transcript-encoding polynucleotide is measured in plants comprising SEQ ID NO:3 and compared to control plants lacking SEQ ID NO:3. Examples of such traits which can be measured and compared in this manner include improved abiotic stress, biotic stress, architecture, photosynthesis, or resource partitioning. Improvements in such traits can be assessed by comparing any measure of the trait itself (e.g., water use efficiency, disease resistance, reduced stature, improved photosynthesis, or nitrogen use efficiency) or a proxy for the trait (e.g., yield of seed and/or other biomass in kg/hectare) in plants comprising SEQ ID NO:3 and compared to control plants lacking SEQ ID NO:3. In certain embodiments, increased expression of the encoded transcript itself is directly measured by determining amounts of the transcript (e.g., an mRNA or non-coding RNA) in plants comprising SEQ ID NO:3 and compared to determining amounts of the transcript-encoding polynucleotide in control plants lacking SEQ ID NO:3. Amounts of the transcript can be determined by a variety of techniques including PCR (e.g., quantitative reverse-transcriptase PCR; qRT-PCR), hybridization, CRISPR-, and/or sequencing-based techniques (Khodakov et al., doi.org/10.1016/j.addr.2016.04.005; Gootenberg, et al. doi: 10.1126/science.aaq0179). In certain embodiments, expression of a transcript-encoding polynucleotide can also be determined by measuring amounts of a protein encoded by a transcript in plants comprising and compared to amounts of the protein control plants lacking SEQ ID NO:3. Amounts of the protein can be determined by a variety of techniques including enzymatic assays (e.g., where the protein is an enzyme), immuno-, and mass spectroscopy based techniques (Chen et al. doi: 10.1186/s12967-015-0537-6; Bruce et al. doi: 10.1002/0471250953.bi1321s41). The magnitude of the increase in transcript production may depend on the baseline expression level of the unmodified endogenous transcript-encoding polynucleotide in the respective cells or tissues. By way of a non-limiting example, the magnitude of the increase in expression of an endogenous gene modified by insertion or formation of SEQ ID NO: 3 over baseline expression levels of the unmodified endogenous gene will be greatest where baseline expression levels are low. In certain embodiments, expression of the endogenous gene modified by insertion or formation of SEQ ID NO: 3 can be increased by at least 1.2-, 1.5-, 2-, 3-, 4-, or 5-fold over baseline expression levels of the unmodified endogenous gene. In certain embodiments, expression of the endogenous gene modified by insertion or formation of SEQ ID NO: 3 can be increased by at least about 1.2- or 1.5-fold to about 2-, 3-, 4-, 5-, 6-fold or more over baseline expression levels of the unmodified endogenous gene.

In certain embodiments, it will be desirable to use genome editing molecules to introduce or form SEQ ID NO:3 in a plant genome. Gene editing molecules of use in methods provided herein include molecules capable of introducing a double-strand break ("DSB") or single-strand break ("SSB") at a specific site or sequence in a double-stranded DNA, such as in genomic DNA or in a target gene located within the genomic DNA as well as accompanying guide RNA or donor or other DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for use with an RNA-guided nuclease, or a DNA encoding a gRNA for use with an RNA-guided nuclease; (d) donor DNA template polynucleotides suitable for insertion at a break in genomic DNA by homology-directed repair (HDR) or microhomology-mediated end joining (MMEJ); and (e) other DNA templates (e.g., dsDNA, ssDNA, or combinations thereof) suitable for insertion at a break in genomic DNA (e.g., by non-homologous end joining (NHEJ).

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). In certain embodiments, an RNA-guided endonuclease that leaves a blunt end following cleavage of the target site is used. Blunt-end cutting RNA-guided endonucleases include Cas9, Cas12c, Cas12i, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e. All of the patent publications referenced in this paragraph are incorporated herein by reference in their entirety.

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) to form an RNA-guided endonuclease/guide RNA complex which can specifically bind sequences in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins. In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) Nature Rev. Genet., 11:636-646; Mohanta et al. (2017) Genes vol. 8,12: 399; Ramirez et al. Nucleic Acids Res. (2012); 40(12): 5560-5568; Liu et al. (2013) Nature Communications, 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described and can be adapted for use in the methods described herein; see, e.g., Guo et al. (2010) J. Mol. Biol., 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) Genes vol. 8,12: 399). TALE nickases have also been described and can be adapted for use in methods described herein (Wu et al.; Biochem Biophys Res Commun. (2014); 446(1):261-6; Luo et al; Scientific Reports 6, Article number: 20657 (2016)).

In certain embodiments where SEQ ID NO:3 is inserted into the genome at a site of a double stranded break in the plant genome introduced by one or more nucleases or nickases (e.g., a CRISPR/guide RNA complex with site-specific endonuclease or nickase, an aZF nuclease or nickase, and/or a TALE nuclease or nickase), the donor DNA template or other DNA template comprises SEQ ID NO:3. In certain embodiments where SEQ ID NO:3 is formed in the genome at a site of a double stranded break in the plant genome introduced by a nuclease, the donor DNA template or other DNA template can comprise less than the complete set of 36 nucleotides or base pairs of SEQ ID NO:3 sequence and genomic DNA at the site of integration can contribute the nucleotides or base pairs of SEQ ID NO:3 that are absent from the donor DNA template or other DNA template. In certain embodiments where SEQ ID NO:3 is formed in the genomic DNA, the donor DNA template or other DNA template can comprise 24 to 35 contiguous nucleotides or base pairs of SEQ ID NO:3, the genomic DNA at the site of integration can contribute 1 to 12 nucleotides or base pairs of the SEQ ID NO:3 sequence which are lacking from the donor DNA template or other DNA template, and the complete 36 base pair sequence of SEQ ID NO:3 is formed at the site of integration in the genome. Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In one embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e.g., 1, 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand of the targeted integration site (in the case of a perfectly base-paired double-stranded polynucleotide molecule). Such donor DNA templates can be integrated in genomic DNA containing blunt and/or staggered double stranded DNA breaks by homology-directed repair (HDR) or microhomology-mediated end joining (MMEJ). In certain embodiments, a donor DNA template homology arm can be about 20, 50, 100, 200, 400, or 600 to about 800, or 1000 base pairs in length. In certain embodiments, a donor DNA template molecule can be delivered to a plant cell in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. In other embodiments, DNA templates suitable for NHEJ insertion will lack homology arms that are partially or completely homologous to genomic DNA (gDNA) sequences flanking a target site-specific endonuclease cleavage site in the gDNA. In certain embodiments, the DNA template comprising all SEQ ID NO:3 (e.g., dsDNA, ssDNA, or combinations thereof) can be inserted at a double-stranded break in gDNA by non-homologous end joining (NHEJ). In certain embodiments, the DNA template comprising less than the complete set of 36 nucleotides or base pairs of SEQ ID NO:3 sequence (e.g., dsDNA, ssDNA, or combinations thereof) can be inserted at a double-stranded break in gDNA by non-homologous end joining (NHEJ), gDNA at the site of insertion can contribute the nucleotides or base pairs of SEQ ID NO:3 that are absent from the DNA template, and SEQ ID NO:3 can be formed at the site of the double-stranded break in the gDNA.

In some embodiments, the enhancer of SEQ ID NO:3 replaces or largely replaces a corresponding sequence in a plant gene, such as in a promoter. Accordingly, a replacement rather than an insertion leaves the positioning of other elements unchanged. A replacement target site may be chosen by similarity to SEQ ID NO: 3. A replacement template could be used in an HDR process, and/or DNA base editing and/or genome editing could be used to produce the desired replacement region that corresponds to SEQ ID NO: 3. Base editors include for example, a site-specific base edit mediated by an C*G to T•A or an A•T to G*C base editing deaminase enzymes (Gaudelli et al., Programmable base editing of A•T to G*C in genomic DNA without DNA cleavage." Nature (2017); Nishida et al. "Targeted nucleotide editing using hybrid prokaryotic and vertebrate adaptive immune systems." Science 353 (6305) (2016); Komor et al. "Programmable editing of a target base in genomic DNA without double-stranded DNA cleavage." Nature 533 (7603) (2016):420-4. Catalytically dead dCas9 fused to a cytidine deaminase or an adenine deaminase protein becomes a specific base editor that can alter DNA bases without inducing a DNA break. Base editors convert C→T (or G→A on the opposite strand) or an adenine base editor that would convert adenine to inosine, resulting in an A→G change within an editing window specified by the gRNA.

Various treatments can be used for delivery of gene editing molecules and/or other molecules to a plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP (ribonucleoprotein)-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., *Azobacter* sp., *Phyllobacterium* sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) *Nature*, 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

Techniques for effecting genome editing in crop plants (e.g., maize), include use of morphogenic factors such as Wuschel (WUS), Ovule Development Protein (ODP), and/or Babyboom (BBM) which can improve the efficiency of recovering plants with desired genome edits. In some aspects, the morphogenic factor comprises WUS1, WUS2, WUS3, WOX2A, WOX4, WOX5, WOX9, BBM2, BMN2, BMN3, and/or ODP2. In certain embodiments, compositions and methods for using WUS, BBM, and/or ODP, as well as other techniques which can be adapted for effecting genome edits in plant and other germplasm, are set forth in US 20030082813, US 20080134353, US 20090328252, US 20100100981, US 20110165679, US 20140157453, US 20140173775, and US 20170240911, which are each incorporated by reference in their entireties. In certain embodiments, the genome edits can be effected in regenerable plant parts (e.g.; plant embryos) of crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

An expression enhancing element comprising SEQ ID NO:3 can be operably linked to an exogenous (i.e., transgene encoded) or endogenous transcript-encoding genes that include those conferring traits such as improved yield, improved food and/or feed characteristics (e.g., improved oil, starch, protein, or amino acid quality or quantity), improved nitrogen use efficiency (e.g., a glutamine synthetase gene), improved biofuel use characteristics (e.g., improved ethanol production), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and/or increased meristem size) in comparison to a control plant lacking the targeted genetic change. Polynucleotides comprising SEQ ID NO:3 can be operably linked to such genes by insertions of polynucleotides in the plant genome that result in the insertion or formation of SEQ ID NO:3 in an endogenous plant gene. Sites in endogenous plant genes suitable for insertion or formation of SEQ ID NO:3 include promoter, coding, and non-coding regions (e.g., 5' UTRs, introns, and 3' UTRs). Target plants suitable for insertion or formation of SEQ ID NO: 3 include plants and plant cells of any species of interest, including dicots and monocots. Plants of interest include row crop plants, fruit-producing plants and trees, vegetables, trees, and ornamental plants including ornamental flowers, shrubs, trees, groundcovers, and turf grasses. Examples of commercially important cultivated crops, trees, and plants include: alfalfa (*Medicago sativa*), almonds (*Prunus dulcis*), apples (*Malus* x *domestica*), apricots (*Prunus armeniaca, P. brigantine, P. mandshurica, P. mume, P. sibirica*), asparagus (*Asparagus officinalis*), bananas (*Musa* spp.), barley (*Hordeum vulgare*), beans (*Phaseolus* spp.), blueberries and cranberries (*Vaccinium* spp.), cacao (*Theobroma cacao*), canola and rapeseed or oilseed rape, (*Brassica napus*), carnation (*Dianthus caryophyllus*), carrots (*Daucus carota sativus*), cassava (*Manihot esculentum*), cherry (*Prunus avium*), chickpea (*Cider arietinum*), chicory (*Cichorium intybus*), chili peppers and other *capsicum* peppers (*Capsicum annuum, C. frutescens, C. chinense, C. pubescens, C. baccatum*), chrysanthemums (*Chrysanthemum* spp.), coconut (*Cocos nucifera*), coffee (*Coffea* spp. including *Coffea arabica* and *Coffea canephora*), cotton (*Gossypium hirsutum* L.), cowpea (*Vigna unguiculata*), cucumber (*Cucumis sativus*), currants and gooseberries (*Ribes* spp.), eggplant or aubergine (*Solanum melongena*), eucalyptus (*Eucalyptus* spp.), flax (*Linum usitatissumum* L.), geraniums (*Pelargonium* spp.), grapefruit (*Citrus* x *paradisi*), grapes (*Vitus* spp.) including wine grapes (*Vitus vinifera*), guava (*Psidium guajava*), hops (*Humulus lupulus*), hemp and cannabis (*Cannabis sativa* and *Cannabis* spp.), irises (*Iris* spp.), lemon (*Citrus limon*), lettuce (*Lactuca sativa*), limes (*Citrus* spp.), maize (*Zea mays* L.), mango (*Mangifera indica*), mangosteen (*Garcinia mangostana*), melon (*Cucumis melo*), millets (*Setaria* spp, *Echinochloa* spp, *Eleusine* spp, *Panicum* spp., *Pennisetum* spp.), oats (*Avena sativa*), oil palm (*Ellis quineensis*), olive (*Olea europaea*), onion (*Allium cepa*), orange (*Citrus sinensis*), papaya (*Carica papaya*), peaches and nectarines (*Prunus persica*), pear (*Pyrus* spp.), pea (*Pisa sativum*), peanut (*Arachis hypogaea*), peonies (*Paeonia* spp.), petunias (*Petunia* spp.), pineapple (*Ananas comosus*), plantains (*Musa* spp.), plum (*Prunus domestica*), poinsettia (*Euphorbia pulcherrima*), Polish canola (*Brassica rapa*), poplar (*Populus* spp.), potato (*Solanum tuberosum*), pumpkin (*Cucurbita pepo*), rice (*Oryza sativa* L.), roses (*Rosa* spp.), rubber (*Hevea brasiliensis*), rye (*Secale cereale*), safflower (*Carthamus tinctorius* L), sesame seed (*Sesame indium*), sorghum (*Sorghum bicolor*), soybean (*Glycine max* L.), squash (*Cucurbita pepo*), strawberries (*Fragaria* spp., *Fragaria* x *ananassa*), sugar beet (*Beta vulgaris*), sugarcanes (*Saccharum* spp.), sunflower (*Helianthus annus*), sweet potato (*Ipomoea batatas*), tangerine (*Citrus tangerina*), tea (*Camellia sinensis*), tobacco (*Nicotiana tabacum* L.), tomato (*Lycopersicon esculentum*), tulips (*Tulipa* spp.), turnip (*Brassica rapa rapa*), walnuts (*Juglans* spp. L.), watermelon (*Citrulus lanatus*), wheat (*Tritium aestivum*), and yams (*Discorea* spp.).

General categories of genes of interest include, but are not limited to, those genes involved in information, such as transcription factors including zinc finger-containing transcription factors, those involved in communication, such as kinases and/or other signal-transduction factors, and those involved in housekeeping, such as heat shock proteins. More specific categories, for example, include, but are not limited to, genes encoding important traits for agronomics (e.g., increased yield, improved nitrogen use efficiency), abiotic stress tolerance (e.g., increased water use efficiency, heat, cold, and drought tolerance), abiotic stress tolerance (e.g., insect resistance, fungal or bacterial disease resistance, and nematode resistance), herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Disease and/or insect resistance genes may encode resistance to pests that have great yield drag such as for example, Northern Corn Leaf Blight, head smut, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. *Glycinea*. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from

*Bacillus licheniformis* that was optimized by gene shuffling for acetylation of the broad spectrum herbicide, glyphosate, forming the basis of a novel mechanism of glyphosate tolerance in transgenic plants (Castle et al. (2004) Science 304, 1 151-1 154).

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

In certain embodiments, the present disclosure contemplates the insertion of the enhancer sequence into a recipient cell at more than one advantageous locus.

Commodity plant products obtained from plants or plant parts comprising SEQ ID NO:3 as well as methods for making such products are provided. In certain embodiments, the commodity products are processed products are made from the plant or its seeds, including: (a) corn, soy, cotton, or canola seed meal (defatted or non-defatted); (b) extracted proteins, oils, sugars, syrups, and starches; (c) fermentation products; (d) animal feed or human food products (e.g., feed and food comprising corn, soy, cotton, or canola seed meal (defatted or non-defatted) and other ingredients (e.g., other cereal grains, other seed meal, other protein meal, other oil, other starch, other sugar, a binder, a preservative, a humectant, a vitamin, and/or mineral); (e) a pharmaceutical; (f) raw or processed biomass (e.g., cellulosic and/or lignocellulosic material; silage); and (g) various industrial products.

Also provided herein are methods for detecting SEQ ID NO:3 in any of the aforementioned biological samples and commodity products. Detection of the DNA molecules comprising SEQ ID NO:3 can be achieved by any combination of nucleic acid amplification (e.g., PCR amplification), hybridization, sequencing, and/or mass-spectrometry based techniques. Methods set forth for detecting foreign nucleic acids in transgenic loci set forth in US 20190136331 and U.S. Pat. No. 9,738,904, both incorporated herein by reference in their entireties, can be adapted for use in detection of the nucleic acids provided herein. In certain embodiments, such detection is achieved by amplification and/or hybridization-based detection methods using a method (e.g., selective amplification primers) and/or probe (e.g., capable of selective hybridization or generation of a specific primer extension product) which specifically recognizes the target DNA molecule (e.g., transgenic locus excision site) but does not recognize DNA from an unmodified transgenic locus. In certain embodiments, the hybridization probes (e.g., polynucleotides comprising at least 15 to 36 nucleotides of SEQ ID NO:3) can comprise detectable labels (e.g., fluorescent, radioactive, epitope, and chemiluminescent labels). In certain embodiments, a single nucleotide polymorphism detection assay can be adapted for detection of the target DNA molecule (e.g., a SEQ ID NO:3 insertion or formation site in a plant genome).

Inbred and hybrid plants and seeds comprising SEQ ID NO:3 operably linked to a transcript-encoding polynucleotide are provided herein along with methods for making and using such hybrid and inbred seed. Methods for inbred seed production include selfing inbred plants and restricting cross-pollination by any plants other than the inbred plant. Methods for production of such hybrid seed can comprise crossing elite crop plant lines where at least one of the pollen donor or recipient comprises SEQ ID NO:3 operably linked to a transcript-encoding polynucleotide. In certain embodiments, the pollen donor and recipient will comprise germplasm of distinct heterotic groups and provide hybrid seed and plants exhibiting heterosis. In certain embodiments, the inbred plant, the hybrid plant, the pollen donor and/or the pollen recipient can each comprise a distinct transgenic locus which confers either a distinct trait (e.g., herbicide tolerance or insect resistance), a different type of trait (e.g., tolerance to distinct herbicides or to distinct insects such as coleopteran or lepidopteran insects), or a different mode-of-action for the same trait (e.g., resistance to coleopteran insects by two distinct modes-of-action or resistance to lepidopteran insects by two distinct modes-of-action). Transgenes that can be introduced into the plant lines comprising SEQ ID NO:3 operably linked to a transcript-encoding polynucleotide by breeding or by direct transformation include: (i) transgenes that confer insect resistance (e.g., transgenes that produce *Bacillus thuringiensis* proteins including Cry1Ab, Cry1Ac, Cry1F, Cry2Ab, Cry2Ae, Cry3A, Cry3Bb, Cry9c, Cry34, Cry35, VIP3A, and variants thereof; transgenes that induce insect-inhibitory RNAi responses including dvsnf7); and (ii) transgenes that confer herbicide tolerance (e.g., CP4-EPSPS or other EPSPS genes which confer glyphosate tolerance; PAT or BAR genes which confer resistance to glufosinate herbicides; aad-1 genes which confer resistance to 2,4-D and aryloxyphenoxypropionate herbicides; DMO genes which confer resistance to dicamba herbicide). Examples of selected transgenic corn, soybean, cotton, and canola plant events which contain transgenes that confer traits such as herbicide tolerance and/or pest tolerance are disclosed in U.S. Pat. Nos. 7,323,556, 8,575,434, 6,040,497, 10,316,330; 8,618,358, 8,212,113, 9,428,765, 8,455,720, 7,897,748, 8,273,959, 8,093,453, 8,901,378, 8,466,346, RE44,962, 9,540,655, 9,738,904, 8,680,363, 8,049,071, 9,447,428, 9,944,945, 8,592,650, 10,184,134, 7,179,965, 7,371,940, 9,133,473, 8,735,661, 7,381,861, 8,048,632, and 9,738,903, incorporated herein by reference in their entireties. Transgenes that can be used to confer insect resistance in maize include those disclosed in US Patent Application Publication Nos. 20150361446 and 20200190533, incorporated herein by reference in their entireties, as well as those disclosed in U.S. Pat. Nos. 6,342,660, 6,852,915, 7,323,556, 7,695,914, 7,705,216, 7,897,748, 8,212,113, 8,455,720, 8,466,346, 8,575,434, 8,901,378, 9,428,765, and 10316330, incorporated herein by reference in their entireties. Transgenes that can be used to confer herbicide tolerance in maize include those disclosed in US Patent Application Publication Nos. 20120244533 and 20200190533, incorporated herein by reference in their entireties, as well as those disclosed in U.S. Pat. Nos. 6,040,497, 6,852,915, 8,273,959, 8,618,358, 8,759,618, and 9,994,863, incorporated herein by reference in their entireties. In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the crop plants provided herein are described in Wan et al. Molecular Plant; 12, 3, (2019):321-342 as well as in U.S. Pat. No. 8,618,358; US 20130031674; and US 2003188347.

In certain embodiments, plants provided herein which comprise SEQ ID NO: 3 can further comprise one or more targeted genetic changes introduced by one or more of gene editing molecules or systems. Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by reference in its entirety, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (1) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target maize genes that can be subjected to targeted gene edits to confer useful traits include: (a) ZmIPK1 (herbicide tolerant and phytate reduced maize; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMSS (thermosensitive male sterile; Li et al. J Genet Genomics. 2017; 44:465-8); (f) ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target soybean genes that can be subjected to targeted gene edits to confer useful traits include: (a) FAD2-1A, FAD2-1B (increased oleic acid content; Haun et al.; Plant Biotechnol J. 2014; 12:934-40); (b) FAD2-1A, FAD2-1B, FAD3A (increased oleic acid and decreased linolenic content; Demorest et al., BMC Plant Biol. 2016; 16:225); and (c) ALS (herbicide tolerance; Svitashev et al.; Plant Physiol. 2015; 169:931-45). A non-limiting examples of target *Brassica* genes that can be subjected to targeted gene edits to confer useful traits include: (a) the FRIGIDA gene to confer early flowering (Sun Z, et al. J Integr Plant Biol. 2013; 55:1092-103); and (b) ALS (herbicide tolerance; US 20160138040, incorporated herein by reference in its entirety). Non-limiting examples of target genes in crop plants including corn and soybean which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210). In certain embodiments, such targeted genetic changes can be combined with plants which comprise SEQ ID NO: 3 by breeding techniques. Such breeding techniques include crossing and/or introgression by back-crossing to a recurrent parent. In such crosses, the plants which comprise SEQ ID NO: 3 can be either a pollen donor or recipient. In certain embodiments, plants which comprise SEQ ID NO: 3 can be used as the recurrent parent in such backcrosses to introgress the targeted genetic change into plant germplasm comprising SEQ ID NO: 3. In certain embodiments, plants which comprise the target genetic change(s) can be used as the recurrent parent in such backcrosses to introgress the genomic region comprising SEQ ID NO: 3 into plant germplasm comprising the target genetic change(s).

In certain embodiments, plants provided herein which comprise SEQ ID NO: 3 can further comprise one or more genetic loci conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Sources of such genetic loci include elite cultivars, sexually compatible wild relatives (e.g., *Glycine soja*), plant germplasm which has been subjected to random mutagenesis (e.g., with a chemical mutagen such as EMS or with gamma-ray mutagenesis), and the like. In certain embodiments, such genetic loci can be combined with plants which comprise SEQ ID NO: 3 by breeding techniques. Such breeding techniques include crossing and/or introgression by backcrossing to a recurrent parent. In such crosses, the plants which comprise SEQ ID NO: 3 can be either a pollen donor or recipient. In certain embodiments, plants which comprise SEQ ID NO: 3 can be used as the recurrent parent in such backcrosses to introgress the genetic locus into plant germplasm comprising SEQ ID NO: 3. In certain embodiments, plants which comprise the genetic locus or loci can be used as the recurrent parent in such backcrosses to introgress the genomic region comprising SEQ ID NO: 3 into plant germplasm comprising genetic locus or loci.

Also provided herein are methods for producing a commodity plant product or plant material comprising growing any of the aforementioned plants comprising SEQ ID NO:3 or growing plants from seeds comprising SEQ ID NO:3. In certain embodiments, such plants and/or seeds are irrigated, fertilized, and/or treated with a biological agent (e.g., a plant beneficial microorganism including a *Bacillus* sp., a *Rhizobium* sp., and the like), nematicide (e.g., a carbamate or organophosphate insecticide), insecticide (e.g., an neonicotinoid, pyrethroid, carbamate, or organophosphate insecticide) and/or fungicide (e.g., a benzimidazole, imidazole, or strobilurin fungicide). Plants can be treated with such fertilizers, biological agents, nematicides, insecticides, and fungicides by methods including spraying, fumigating, and/or soil drenching. Seeds can be treated with such fertilizers, biological agents, nematicides, insecticides, and fungicides by methods including in-furrow applications or by coating (e.g., with a drum coater, rotary coater, tumbling drum, fluidized bed, and/or spouted bed apparatus). Methods and compositions including various binders, fillers, film coats, and active ingredients such as fertilizers, surfactants, plant growth regulators, crop desiccants, fungicides, bacteriocides, bacteriostats, insecticides, and insect repellants for coating seeds that can be adapted for use with seeds provided herein are disclosed in U.S. patent Ser. No. 10/745,578, which is incorporated herein by reference in its entirety.

Embodiments

Various embodiments of the DNA molecules, plants, plant parts, genomes, chromosomes, methods, biological samples, and other compositions described herein are set forth in the following set of numbered embodiments.

1. A DNA molecule comprising the polynucleotide sequence of SEQ ID NO:3.

2. The DNA molecule of embodiment 1, wherein the DNA molecule is an isolated, synthetic, and/or recombinant DNA molecule.

3. The DNA molecule of embodiment 1 or 2, wherein the polynucleotide sequence of SEQ ID NO:3 is operably linked to a polynucleotide sequence comprising a promoter, optionally wherein the promoter is an endogenous promoter, and optionally wherein the endogenous promoter is located in a plant chromosome.

4. The DNA molecule of embodiment 1, 2, or 3, wherein the polynucleotide sequence of SEQ ID NO:3 and the promoter are operably linked to a transcription unit and increase expression of a transcript or protein encoded by the transcription unit in a plant cell relative to a control plant cell comprising the promoter in the absence of the polynucleotide sequence of SEQ ID NO:3.

5. The DNA molecule of any one of embodiments 1-4, wherein the polynucleotide sequence of SEQ ID NO:3 is located about 10, 20, 30, or 40 base pairs (bp) to about 100, 240, 300, 400, 500, 1000, 2000, 3000, or 5000 bp of the transcriptional start site of the transcription unit.

6. The DNA molecule of any one of embodiments 1-5, wherein the promoter is an endogenous plant promoter and the transcription unit is an endogenous plant transcription unit, wherein the promoter and the transcription unit are located in a plant chromosome, and optionally wherein the endogenous plant promoter and endogenous plant transcription unit element is a maize, soybean, cotton, or canola plant promoter and transcription unit.

7. A biological sample comprising the DNA molecule of any one of embodiments 1 to 6.

8. The biological sample of embodiment 7, wherein the sample comprises maize, soybean, cotton, or canola seed meal.

9. A plant chromosome comprising the DNA molecule of any one of embodiments 1 to 6, optionally wherein the plant chromosome is a maize, soybean, cotton, or canola plant chromosome.

10. The plant chromosome of embodiment 9, wherein the plant chromosome is a maize plant chromosome.

11. The plant chromosome of embodiment 9 or 10, wherein one or more nucleotides of SEQ ID NO:3 are endogenous nucleotides of the plant chromosome, optionally wherein at least 24 nucleotides of SEQ ID NO:3 are exogenous nucleotides inserted in the plant chromosome.

12. A plant cell comprising the DNA molecule of any one of embodiments 1 to 6, optionally wherein the plant cell is a maize, soybean, cotton, or canola plant cell.

13. The plant cell of embodiment 12, wherein the polynucleotide sequence of SEQ ID NO:3 is operably linked to a polynucleotide sequence comprising a promoter, wherein the promoter is an endogenous promoter, and wherein the endogenous promoter is located in a plant chromosome.

14. The plant cell of embodiment 12 or 13, wherein the plant cell is a maize plant cell.

15. A tissue culture of regenerable cells comprising the plant cell of embodiment 12.

16. A plant comprising the DNA molecule of any one of embodiments 1 to 6, optionally wherein the plant is a maize, soybean, cotton, or canola plant.

17. The plant of embodiment 16, wherein the plant is a maize, soybean, cotton, or canola plant.

18. The plant of embodiment 16 or 17, wherein the polynucleotide sequence of SEQ ID NO:3 is operably linked to a polynucleotide sequence comprising a promoter, wherein the promoter is an endogenous promoter, and wherein the endogenous promoter is located in a plant chromosome.

19. A plant part comprising the DNA molecule of any one of embodiments 1 to 6, optionally wherein the plant part is a maize, soybean, cotton, or canola plant part.

20. The plant part of embodiment 19, wherein the plant part is a maize plant part.

21. The plant part of embodiment 19 or 20, wherein the plant part is a seed, optionally wherein the seed is a maize seed.

22. The plant part of embodiment 19, 20, or 21, wherein the seed is hybrid seed, optionally wherein the hybrid seed is F1 hybrid seed, and optionally wherein the F1 hybrid seed exhibits heterosis.

23. The plant part of any one of embodiments 19-22, wherein the seed is inbred seed.

24. A method of plant seed production, said method comprising crossing the plant of any one of embodiments 16-18 with a second plant to produce plant seed and optionally harvesting the seed.

25. The method of embodiment 24, wherein the genotype of the plant and the genotype of the second plant are of different genotypes and the seed is hybrid seed.

26. The method of embodiment 24 or 25, wherein the plant or the second plant further comprise a transgene, a targeted genetic change, or genetic locus conferring a desired trait and the harvested seed comprise the transgene, targeted genetic change, or genetic locus.

27. A method of plant seed production, said method comprising selfing the plant of any one of embodiments 16-18 to produce plant seed and optionally harvesting the seed.

28. The method of embodiment 27, wherein the plant and the seed are inbred.

29. A method of producing a plant comprising an added desired trait, said method comprising introducing a transgene, a targeted genetic change, or genetic locus conferring the desired trait into the plant of embodiment 16, 17, or 18.

30. A method of producing a commodity plant product, said method comprising processing a plant or seed comprising the DNA molecule of any one of embodiments 1 to 6 and recovering the commodity plant product from the processed plant or seed.

31. The method of embodiment 30, commodity plant product is seed meal, starch, syrup, silage, oil, or protein.

32. The method of embodiment 30 or 31, wherein the commodity plant product comprises a detectable amount of the DNA molecule.

33. A method of producing plant material, the method comprising growing a plant having an expression increasing element comprising SEQ ID NO:3 operably linked to a transcript-encoding polynucleotide, wherein the expression of the transcript-encoding polynucleotide in said plant is increased when compared to a control plant lacking the expression increasing element.

34. The method of embodiment 33, wherein growing comprises at least one of sowing a seed which germinates and forms the plant, irrigating the seed or plant, and/or treating the plant or the seed with a biological agent, herbicide, insecticide, or fungicide.

35. A method of producing plant material, the method comprising:
(a) providing a plant having an expression increasing element comprising SEQ ID NO:3 operably linked to a transcript-encoding polynucleotide, wherein the expression of the transcript-encoding polynucleotide is increased in said plant when compared to a control plant lacking the expression increasing element; and,
(b) growing the plant under conditions that allow for expression of the transcript promoting polynucleotide.

36. The method of any one of embodiments 33 to 35, wherein the plant material comprises a seed, optionally wherein the method further comprises harvesting the seed from the plant.

37. The method of any one of embodiments 33 to 36, wherein the expression increasing element is in an endogenous promoter which is operably linked to the transcript encoding polynucleotide or in a 5' UTR, intron, or 3' UTR of the transcript encoding polynucleotide and wherein said endogenous promoter, 5' UTR, intron, or 3' UTR is located in a plant chromosome.

38. The method of any one of embodiments 33 to 37, wherein the polynucleotide sequence of SEQ ID NO:3 is located about 10, 20, 30, or 40 base pairs (bp) to about 100, 240, 300, 400, 500, 1000, 2000, 3000, or 5000 bp from the transcriptional start site of the transcription unit.

39. The method of any one of embodiments 33 to 38, wherein the transcript-encoding polynucleotide is an endogenous plant transcription unit, wherein the promoter and the transcription unit are located in a plant chromosome, optionally wherein the transcript-encoding polynucleotide is a maize, soybean, cotton, or canola plant transcript-encoding polynucleotide.

40. The method of any one of embodiments 33 to 39, wherein the plant is a maize plant and/or wherein the seed is a maize plant seed.

41. Method of identifying a biological sample comprising a polynucleotide comprising a modified plant gene, comprising the step of detecting the presence of SEQ ID NO:3 in the biological sample.

42. The method of embodiment 41, wherein the biological sample is obtained from a plant cell, plant, or plant part, optionally wherein the plant part is a seed, and/or optionally wherein the plant is a maize, soybean, cotton, or canola plant.

43. A method for producing nucleic acids comprising the polynucleotide sequence of SEQ ID NO:3, the method comprising isolating nucleic acids from the plant of embodiment 16, 17, or 18 or from the plant part of any one of embodiments 19-23.

44. A method of producing a treated plant seed comprising contacting a seed comprising the DNA molecule of any one of embodiments 1 to 6 with a composition comprising a biological agent, nematicide, insecticide, or fungicide.

45. The method of embodiment 44, wherein the seed is a maize, soybean, cotton, or canola plant seed.

46. A method of increasing the expression of a polynucleotide sequence in a plant, the method comprising expressing a polynucleotide sequence that is operably linked to an expression increasing element comprising SEQ ID NO:3 and to a promoter, wherein the expression of the polynucleotide is increased in comparison to a control plant lacking the expression increasing element.

47. The method of embodiment 46, wherein the plant is a maize, soybean, cotton, or canola plant, optionally wherein the polynucleotide sequence comprises a gene which confers improved yield, improved food and/or feed characteristics (e.g., improved oil, starch, protein, or amino acid quality or quantity), improved nitrogen use efficiency, improved biofuel use characteristics (e.g., improved ethanol production), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and/or increased meristem size.

48. The method of embodiment 46 or 47, wherein the expression is increased in a part of the plant, optionally wherein the part is a seed, leaf, stem, flower, root, stem, or cell.

49. Use of the DNA molecule of any one of embodiments 1 to 6 to: (i) increase expression of one or more elements encoded by a transcription unit which is operably linked to the promoter in a plant; (ii) confer a useful trait to a plant comprising the DNA molecule or recombinant DNA molecule, wherein the useful trait is optionally improved yield, improved food and/or feed characteristics (e.g., improved oil, starch, protein, or amino acid quality or quantity), improved nitrogen use efficiency, improved biofuel use characteristics (e.g., improved ethanol production), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and/or increased meristem size relative to a control plant lacking the recombinant DNA molecule; (iii) obtain a plant or seed therefrom exhibiting the useful trait of (ii); or (iv) to grow a population of plants exhibiting the useful trait of (ii); optionally wherein the plant of (i), (ii), (iii), or (iv) is a maize, soybean, cotton, or canola plant; or optionally wherein the seed of (iii) is a maize, soybean, cotton, or canola plant.

EXAMPLES

Example 1

Insertion of the transcription enhancing element into a single target in maize protoplasts by NHEJ is illustrated in this example. Maize protoplasts were prepared using established methods (see US20190352655, which is incorporated herein by reference in its entirety).

Maize protoplasts were isolated from leaf material from B104 seedlings, and transfected with double-stranded oligos and RNPs consisting of Cas9 protein complexed with a tracrRNA:crRNA duplex targeting the ZmGln1-3 promoter (crRNA sequence: UACACGUACGAUUACAACCAGU UUUAGAGCUAUGCU; SEQ ID NO:5) and the double stranded oligos described below. The Cas9/tracrRNA/crRNA complex results in a double-stranded break in the DNA 66 bp upstream of the transcription start site of ZmGln1-3 (i.e., the Zm00001d017958 gene according to the B73v4 maize genome encoding the polypeptide of SEQ ID NO:6). Three types of double-stranded oligos were tested: a 24 nt configuration containing two repeats of the enhancer sequence, a 36 bp configuration containing three repeats of the enhancer sequence, and a 48 nt configuration containing four repeats of the enhancer sequence. The oligos were 5' phosphorylated, and contained two phosphorothioate bonds at both ends. As a control, protoplasts were transfected with only RNPs, i.e. without added oligos. Each transfection was performed in triplicate. After transfection, cells were washed, and incubated for 48 hours. At the end of the incubation period, cells were harvested for gDNA and RNA preparation.

To analyze insertion sites, the gDNA was used as template on which PCR was performed with primers flanking the insertion site. After bead clean-up the resulting amplicons were sequenced by next-generation sequencing. Reads were aligned to the target locus, and the percentage of reads containing the enhancer sequence was used as a proxy for the fraction of cells that integrated the enhancer. The data is summarized in FIG. 1. For transfections with the double enhancer, 7% of cells were estimated to have integrated the enhancer element at the Gln1-3 target locus. F or cells transfected with the triple or quadruple enhancer, 44% and 41% respectively of cells had integrated the enhancer element at the target locus. All numbers are averaged across 3 biological replicates. This data shows that the triple element performs the best in terms of insertion efficiency.

Figure 2:
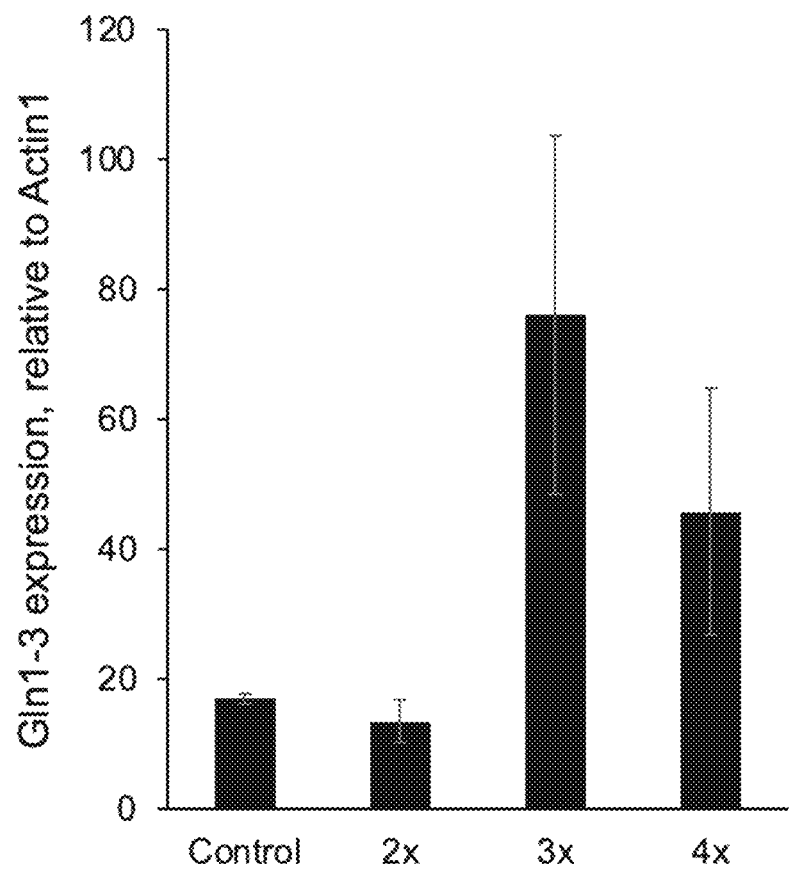
FIG. 2 depicts the effect of a dimer (SEQ ID NO:2), trimer (SEQ ID NO:3), or tetramer (SEQ ID NO:4) of the core element 12 nucleotide sequence (SEQ ID NO:1) inserted into the ZmGln1-3 promoter on ZmGln1-3 expression, compared to controls.

To assess the effect of the inserted enhancer sequence on the expression level of Gln1-3, bulk RNA was extracted from harvested protoplasts, and converted to cDNA. Using qRT-PCR, the expression level of ZmGln1-3 was measured relative to that of ZmAct1, a well-known reference gene; the data is summarized in FIG. 2. In cells transfected with the double enhancer, the expression level of ZmGln1-3 was indistinguishable from control cells transfected with only RNP. However, in cells transfected with the triple enhancer, the expression level of ZmGln1-3 was about 4.5-fold higher compared to controls. For cells transfected with the quadruple enhancer, it was only increased by 2.7-fold. This data indicates that both the triple and quadruple enhancer enhance expression of the target gene when integrated in the promoter, but the triple enhancer does so more efficiently.

Example 2

Enhanced transcription in maize protoplasts at multiple gene targets with the 36 bp enhancer is illustrated in this example. Maize protoplasts were isolated from leaf material from B104 seedlings, and transfected with RNPs consisting of Cas9 complexed with a tracrRNA:crRNA duplex, either with or without double-stranded 5' phosphorylated 36-nt enhancer (SEQ ID NO:3) oligos with two phosphorothioate bonds on both ends with the 36 nucleotide enhancer sequence (SEQ ID NO:3). Three crRNAs were used in this experiment. The first crRNA (UACACGUACGAUUA-CAACCAGUUUUAGAGCUAUGCU; SEQ ID NO:5 targets the ZmGln1-3 promoter (i.e., the promoter of the Zm00001d017958 gene according to the B73v4 maize genome encoding the polypeptide of SEQ ID NO:6). The second crRNA (UGUAUCCGUAUUUAUACGUGGUU UUAGAGCUAUGCU; SEQ ID NO:7) targets the ZmGln1-4 promoter (i.e., the promoter of the Zm 00001d051804 gene according to the B73v4 maize genome encoding the polypeptide of SEQ ID NO:8). The third crRNA (CUCCAAGUGACCGAGCAAGAGUUUUAGAG CUAUGCU; SEQ ID NO:9) targets the ZmLc promoter (i.e., the promoter of the Zm00001d026147 gene according to the B73v4 maize genome encoding the polypeptide of SEQ ID NO:10). Each transfection was performed in triplicate. After transfection, cells were washed, and incubated for 48 hours. At the end of the incubation period, cells were harvested for gDNA and RNA preparation.

To analyze insertion sites, the gDNA was used as template for PCR was performed with primers flanking the insertion site, and after bead clean-up the resulting amplicons were sequenced by next-generation sequencing. Reads were aligned to the target locus, the percentage of reads containing the enhancer sequence was used as a proxy for the fraction of cells that integrated the enhancer. On reads without the enhancer sequence, the number of reads with indels due to NHEJ was determined. The insertion efficiency was in all three cases about half of the total editing efficiency (combining reads with only indels and reads with the oligonucleotide inserted), but the absolute insertion efficiency differed between the targets, and was 31% for ZmGln1-3, 9% for Gln1-4, and 12% for Lc.

Figure 3:
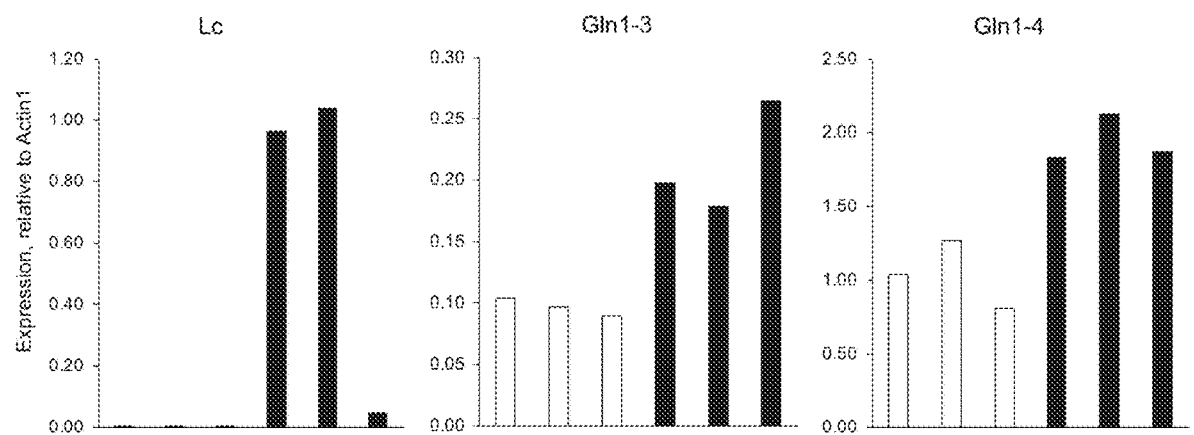
FIG. 3 depicts expression of Lc (first panel), Gln1-3 (middle panel) and Gln1-4 (right panel) in protoplasts with insertion of the 36 bp enhancer (SEQ ID NO:3) in these promoters (black bars), compared to expression in protoplasts without the 36 bp enhancer (white bars). Three biological replicates for each are shown separately.

To assess the effect of the inserted SEQ ID NO:3 enhancer sequence on the expression level of Gln1-3, bulk RNA was extracted from harvested protoplasts, and converted to cDNA. Using qRT-PCR, the expression level of the target gene (ZmGln1-3, ZmGln1-4, or ZmLc) was measured relative to that of ZmAct1, a well-known reference gene. These results are summarized in FIG. 3, showing an increase in expression of Lc by >400-fold, of Gln1-3 by 2.3-fold, and of Gln1-4 by 1.9-fold due to insertion of the maize enhancer sequence in the promoters of these genes. Considering that only a fraction of cells have integrated the enhancer sequence, as discussed above, the increase in gene expression in cells with the enhancer is even higher, indicating that the enhancer works well to increase expression level of multiple targets.

Example 3

Maize genome editing and transformation is illustrated in this example. Immature embryos from a maize line ubiquitously expressing a CRISPR/Cas nuclease in the B104 background were bombarded with gold particles coated with a guide RNA targeting the Gln1-3 promoter in the Gln1.3 gene (i.e., the promoter of the Zm00001d017958 gene according to the B73v4 maize genome encoding the polypeptide of SEQ ID NO:6) and double-stranded 5' phosphorylated oligonucleotides with 2 phosphorothioate bonds at both ends with the 36 nucleotide enhancer sequence (SEQ ID NO:3), and a plasmid encoding the pat resistance gene and a fluorescent protein. Through standard tissue culture practices, with selection for pat resistance and fluorescence, plants were regenerated containing the full or partial 36 bp enhancer element (SEQ ID NO:3). Leaf tissue was taken from regenerated plants for gDNA extraction to check for the presence of the insertion using primers flanking the gRNA target site. An increase in amplicon size allowed selection of events with the insertion present. Amplicon sequencing confirmed that oligo insertion happened at the predicted target sites, which for Gln1-3 was 66 bp upstream of the transcription start site (TSS), with efficiencies ranging from 0.4% to 1.1%, as indicated in Table 1.

TABLE 1

Efficiency of insertion of the triple enhancer element into the ZmGln1.3 promoter through bombardment.

| Experiment | Embryos bombarded | Events regenerated | Events with insertion | % efficiency |
|---|---|---|---|---|
| ZM035 | 271 | 7 | 1 | 0.4% |
| ZM037 | 306 | 4 | 3 | 1.0% |
| ZM041 | 348 | 6 | 4 | 1.1% |
| ZM072 | 454 | 15 | 3 | 0.7% |
| ZM081 | 383 | 3 | 2 | 0.5% |

Figure 4:
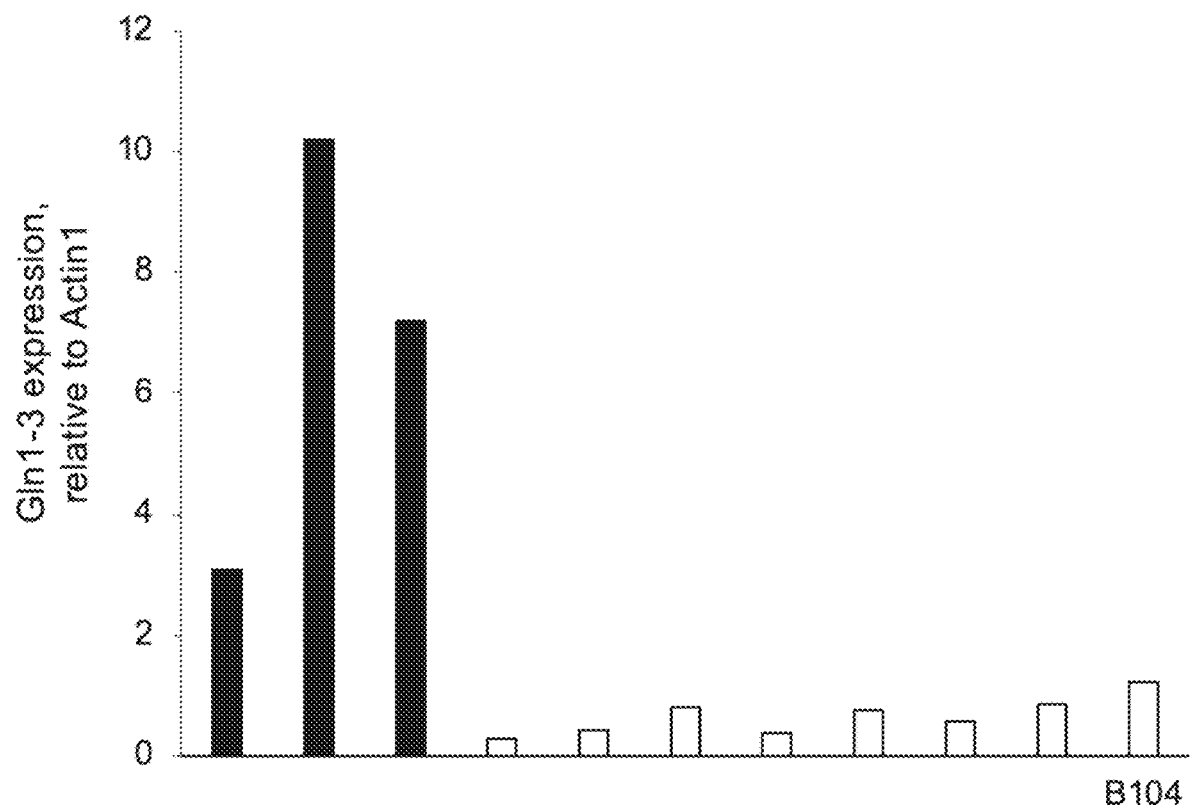
FIG. 4 depicts expression of Gln1-3 (relative to ZmActin1) in T0 events with the 36 bp enhancer insertion (SEQ ID NO:3) in the Gln1-3 promoter (black bar), compared to expression in T0 events without the enhancer insertion or wild-type B104 control (white bars).

RNA was prepared from leaf samples taken from young regenerants from a single bombardment experiment aimed to insert the maize enhancer element in the Gln1-3 promoter, and converted to cDNA. Using SYBR-based qRT-PCR, the expression level of Gln1-3 and the control ZmAct1 were measured. The same plants were also genotyped for the presence of the enhancer. The results are summarized in FIG. 4, showing that plants from events that did not have the enhancer inserted had low levels of Gln1-3, similar to the B104 untransformed control, while plants from events with the 36 bp enhancer element (SEQ ID NO:3) present had levels that were 4-10× higher than controls.

Figure 5:
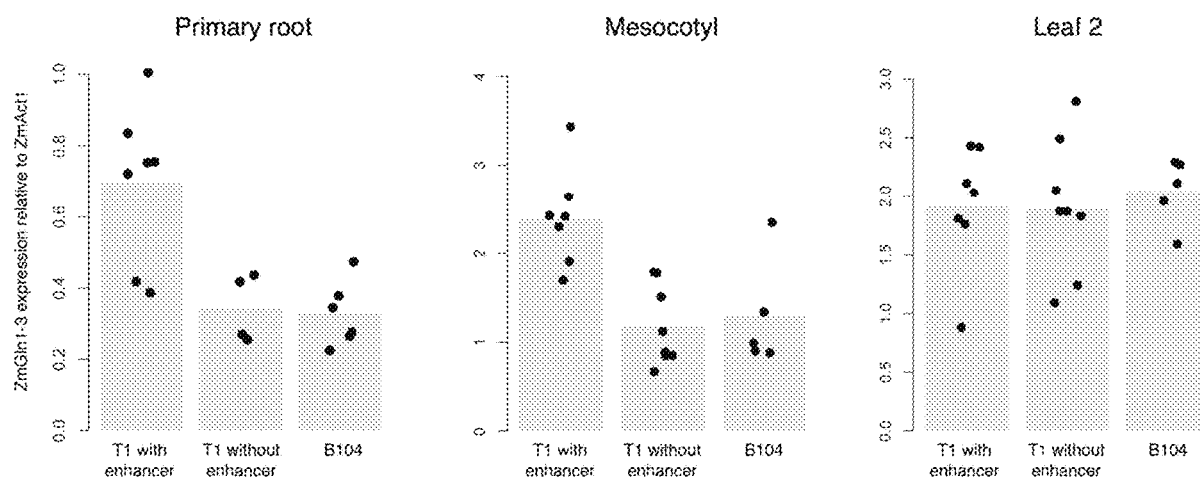
FIG. 5 depicts expression of Gln1-3 (relative to ZmAct1) in T1 individuals with the 36 bp enhancer (SEQ ID NO:3) insertion in the Gln1-3 promoter compared to siblings without the enhancer insertion or wild-types, in primary root, mesocotyl, and root.

Plants containing the insertion were grown to maturity, and crossed to wild-type B104 plants. A T1BC1 population generated in this way coming from a plant heterozygous for the full-length 36 bp enhancer insertion was then grown for further analysis. From these plants, leaf tissue was sampled for genotyping for the insertion by PCR, and leaf, mesocotyl, and primary root tissue was harvested for RNA extraction, cDNA synthesis, and qRT-PCR for Gln1-3 and ZmAct1. The results of these experiments are shown in FIG. 5. Individuals with the insertion were compared to siblings that did not inherit the enhancer insertion allele, and to wild-type B104 plants grown alongside the T1BC1 plants. In both roots and mesocotyl there was a 2-fold and significant ($p<0.05$, two-sided Student's t-test) increase of Gln1-3 expression in plants with the insertion compared to siblings without the insertion and to B104 plants. In leaves, no difference in expression could be detected, possibly linked to the fact that Gln1-3 expression is already very high in leaf compared to root and mesocotyl.

The breadth and scope of the present disclosure should not be limited by any of the above-described exemplary embodiments, but should be defined only in accordance with the following claims and their equivalents.

What is claimed is:

1. A DNA molecule comprising the polynucleotide sequence of SEQ ID NO:3.

2. The DNA molecule of claim 1, wherein the DNA molecule is an isolated, synthetic, and/or recombinant DNA molecule.

3. The DNA molecule of claim 1, wherein the polynucleotide sequence of SEQ ID NO:3 is located in a polynucleotide sequence comprising a promoter.

4. The DNA molecule of claim 3, wherein the polynucleotide sequence of SEQ ID NO:3 and the promoter are operably linked to a transcription unit and increase expression of a transcript or protein encoded by the transcription unit in a plant cell relative to a control plant cell comprising the promoter in the absence of the polynucleotide sequence of SEQ ID NO:3.

5. The DNA molecule of claim 4, wherein the polynucleotide sequence of SEQ ID NO:3 is located about 10, 20, 30, or 40 base pairs (bp) to about 100, 240, 300, 400, 500, 1000, 2000, 3000, or 5000 bp of the transcriptional start site of the transcription unit.

6. The DNA molecule of claim 4, wherein the promoter is a plant promoter and the transcription unit is a plant transcription unit, and optionally wherein the plant promoter and endogenous plant transcription unit element is a maize or a soybean plant promoter and transcription unit.

7. A plant cell comprising the DNA molecule of claim 3, wherein the plant cell is optionally a non-regenerable plant cell which is not capable of being regenerated to produce a plant.

8. The plant cell of claim 7, wherein the polynucleotide sequence of SEQ ID NO:3 is located in a polynucleotide sequence comprising a promoter, wherein the promoter is an endogenous promoter, and wherein the endogenous promoter is located in its natural location in the genome of the plant.

9. The plant cell of claim 7, wherein the plant cell is a maize or a soybean plant cell.

10. A plant comprising the DNA molecule of claim 3.

11. The plant of claim 10, wherein the polynucleotide sequence of SEQ ID NO:3 is located in a polynucleotide sequence comprising a promoter, wherein the promoter is an endogenous promoter, and wherein the endogenous promoter is located in its natural location in the genome of the plant a plant chromosome.

12. A plant part comprising the DNA molecule of claim 3.

13. The plant part of claim 12, wherein the plant part is a seed.

14. A method of producing plant material, the method comprising growing a plant having an expression increasing element comprising SEQ ID NO:3 located in a promoter, wherein the expression increasing element of SEQ ID NO:3 and the promoter are operably linked to a transcript-encoding polynucleotide, and wherein the expression of the transcript-encoding polynucleotide in said plant is increased when compared to a control plant lacking the expression increasing element.

15. The method of claim 14, wherein growing comprises at least one of sowing a seed which germinates and forms the plant, irrigating the seed or plant, and/or treating the plant or the seed with a biological agent, herbicide, insecticide, or fungicide.

16. The method of claim 14, wherein the plant material comprises a seed and wherein the method further comprises harvesting the seed from the plant.

17. The method of claim 14, wherein the expression increasing element is located in an endogenous promoter which is operably linked to the endogenous transcript encoding polynucleotide and wherein said endogenous promoter and endogenous transcript encoding polynucleotide are located in their natural location in the genome of the plant.

18. The method of claim 14, wherein the polynucleotide sequence of SEQ ID NO:3 is located about 10, 20, 30, or 40 base pairs (bp) to about 100, 240, 300, 400, 500, 1000, 2000, 3000, or 5000 bp from the transcriptional start site of the transcription unit.

19. The method of claim 17, wherein the plant is a maize or a soybean plant, wherein the endogenous promoter and the endogenous transcript-encoding polynucleotide is an endogenous maize or soybean plant promoter and an endogenous transcript-encoding polynucleotide located in their natural location in the genome of the maize or the soybean plant.

20. The method of claim 14, wherein the plant is a maize or a soybean plant.

21. A method of producing plant material, the method comprising inserting a transcription increasing element of SEQ ID NO: 3 in a promoter of a plant, and growing the plant to produce plant material, wherein the expression increasing element and the promoter are operably linked to a transcript-encoding polynucleotide, and wherein the expression of the transcript-encoding polynucleotide in said plant is increased when compared to a control plant lacking the expression increasing element.

22. The method of claim 21, wherein growing comprises at least one of sowing a seed which germinates and forms the plant, irrigating the seed or plant, and/or treating the plant or the seed with a biological agent, herbicide, insecticide, or fungicide.

23. The method of claim 21, wherein the plant material comprises a seed and wherein the method further comprises harvesting the seed from the plant.

24. The method of claim 21, wherein the expression increasing element is located in an endogenous promoter which is operably linked to the endogenous transcript encoding polynucleotide and wherein said endogenous promoter and endogenous transcript encoding polynucleotide are located in their natural location in the genome of the plant.

25. The method of claim 21, wherein the polynucleotide sequence of SEQ ID NO:3 is located about 10, 20, 30, or 40 base pairs (bp) to about 100, 240, 300, 400, 500, 1000, 2000, 3000, or 5000 bp from the transcriptional start site of the transcription unit.

26. The method of claim 21, wherein the plant is a maize or a soybean plant, wherein the expression increasing element is located in an endogenous maize or soybean promoter which is operably linked to the endogenous transcript encoding polynucleotide, and wherein said endogenous promoter and endogenous transcript encoding polynucleotide are located in their natural location in the genome of the maize or soybean plant.

27. A biological sample comprising the DNA molecule of claim 1, wherein the biological sample is optionally "non-regenerable" and incapable of being regenerated into a plant or plant part.

28. The biological sample of claim 27, wherein the sample comprises maize, soybean, cotton, or canola seed meal.

29. A method of identifying the biological sample of claim 27 comprising a polynucleotide comprising a modified plant gene wherein the polynucleotide sequence of SEQ ID NO:3 is located in a polynucleotide sequence comprising a promoter, comprising the step of detecting the presence of SEQ ID NO:3 in the biological sample.

30. The method of claim 29, wherein the biological sample is obtained from a plant cell, plant, or plant part, optionally wherein the plant part is a seed, and/or optionally wherein the plant is a maize, soybean, cotton, or canola plant.

* * * * *

SEQUENCE LISTING

```
<160> NUMBER OF SEQ ID NOS: 10

<210> SEQ ID NO 1
<211> LENGTH: 12
<212> TYPE: DNA
<213> ORGANISM: Artificial
<220> FEATURE:
<223> OTHER INFORMATION: synthetic

<400> SEQUENCE: 1
gtaagcgctt ac                                                       12

<210> SEQ ID NO 2
<211> LENGTH: 24
```

-continued

<212> TYPE: DNA
<213> ORGANISM: Artificial
<220> FEATURE:
<223> OTHER INFORMATION: synthetic

<400> SEQUENCE: 2
gtaagcgctt acgtaagcgc ttac                                        24

<210> SEQ ID NO 3
<211> LENGTH: 36
<212> TYPE: DNA
<213> ORGANISM: Artificial
<220> FEATURE:
<223> OTHER INFORMATION: synthetic

<400> SEQUENCE: 3
gtaagcgctt acgtaagcgc ttacgtaagc gcttac                           36

<210> SEQ ID NO 4
<211> LENGTH: 48
<212> TYPE: DNA
<213> ORGANISM: Artificial
<220> FEATURE:
<223> OTHER INFORMATION: synthetic

<400> SEQUENCE: 4
gtaagcgctt acgtaagcgc ttacgtaagc gcttacgtaa gcgcttac              48

<210> SEQ ID NO 5
<211> LENGTH: 36
<212> TYPE: RNA
<213> ORGANISM: Artificial
<220> FEATURE:
<223> OTHER INFORMATION: synthetic

<400> SEQUENCE: 5
uacacguacg auuacaacca guuuuagagc uaugcu                           36

<210> SEQ ID NO 6
<211> LENGTH: 356
<212> TYPE: PRT
<213> ORGANISM: Zea mays

<400> SEQUENCE: 6

Met Ala Cys Leu Thr Asp Leu Val Asn Leu Asn Leu Ser Asp Asn Thr
1               5                   10                  15

Glu Lys Ile Ile Ala Glu Tyr Ile Trp Ile Gly Gly Ser Gly Met Asp
            20                  25                  30

Leu Arg Ser Lys Ala Arg Thr Leu Ser Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Cys Tyr Thr
                85                  90                  95

Pro Ala Gly Glu Pro Ile Pro Thr Asn Lys Arg Tyr Asn Ala Ala Lys
            100                 105                 110

Ile Phe Ser Ser Pro Glu Val Ala Ala Glu Glu Pro Trp Tyr Gly Ile
        115                 120                 125

Glu Gln Glu Tyr Thr Leu Leu Gln Lys Asp Thr Asn Trp Pro Leu Gly
    130                 135                 140

-continued

Trp Pro Ile Gly Gly Phe Pro Gly Pro Gln Gly Pro Tyr Tyr Cys Gly
145                 150                 155                 160

Ile Gly Ala Glu Lys Ser Phe Gly Arg Asp Ile Val Asp Ala His Tyr
            165                 170                 175

Lys Ala Cys Leu Tyr Ala Gly Ile Asn Ile Ser Gly Ile Asn Gly Glu
        180                 185                 190

Val Met Pro Gly Gln Trp Glu Phe Gln Val Gly Pro Ser Val Gly Ile
            195                 200                 205

Ser Ser Gly Asp Gln Val Trp Val Ala Arg Tyr Ile Leu Glu Arg Ile
        210                 215                 220

Thr Glu Ile Ala Gly Val Val Thr Phe Asp Pro Lys Pro Ile Pro
225                 230                 235                 240

Gly Asp Trp Asn Gly Ala Gly Ala His Thr Asn Tyr Ser Thr Glu Ser
            245                 250                 255

Met Arg Lys Glu Gly Gly Tyr Glu Val Ile Lys Ala Ala Ile Glu Lys
            260                 265                 270

Leu Lys Leu Arg His Arg Glu His Ile Ala Ala Tyr Gly Glu Gly Asn
        275                 280                 285

Glu Arg Arg Leu Thr Gly Arg His Glu Thr Ala Asp Ile Asn Thr Phe
            290                 295                 300

Ser Trp Gly Val Ala Asn Arg Gly Ala Ser Val Arg Val Gly Arg Glu
305                 310                 315                 320

Thr Glu Gln Asn Gly Lys Gly Tyr Phe Glu Asp Arg Arg Pro Ala Ser
            325                 330                 335

Asn Met Asp Pro Tyr Val Val Thr Ser Met Ile Ala Glu Thr Thr Ile
            340                 345                 350

Ile Trp Lys Pro
        355

<210> SEQ ID NO 7
<211> LENGTH: 36
<212> TYPE: RNA
<213> ORGANISM: Artificial
<220> FEATURE:
<223> OTHER INFORMATION: synthetic

<400> SEQUENCE: 7
uguauccgua uuuauacgug guuuuagagc uaugcu                                    36

<210> SEQ ID NO 8
<211> LENGTH: 356
<212> TYPE: PRT
<213> ORGANISM: Zea mays

<400> SEQUENCE: 8

Met Ala Cys Leu Thr Asp Leu Val Asn Leu Asn Leu Ser Asp Thr Thr
1               5                   10                  15

Glu Lys Ile Ile Ala Glu Tyr Ile Trp Ile Gly Gly Ser Gly Met Asp
            20                  25                  30

Leu Arg Ser Lys Ala Arg Thr Leu Pro Gly Pro Val Thr Asp Pro Ser
        35                  40                  45

Lys Leu Pro Lys Trp Asn Tyr Asp Gly Ser Ser Thr Gly Gln Ala Pro
    50                  55                  60

Gly Glu Asp Ser Glu Val Ile Leu Tyr Pro Gln Ala Ile Phe Lys Asp
65                  70                  75                  80

Pro Phe Arg Arg Gly Asn Asn Ile Leu Val Met Cys Asp Cys Tyr Thr

-continued

```
                    85                  90                  95
Pro Ala Gly Glu Pro Ile Pro Thr Asn Lys Arg Tyr Ser Ala Ala Lys
                100                 105                 110
Ile Phe Ser Ser Leu Glu Val Ala Ala Glu Glu Pro Trp Tyr Gly Ile
            115                 120                 125
Glu Gln Glu Tyr Thr Leu Leu Gln Lys Asp Thr Asn Trp Pro Leu Gly
        130                 135                 140
Trp Pro Ile Gly Gly Phe Pro Gly Pro Gln Gly Pro Tyr Tyr Cys Gly
145                 150                 155                 160
Ile Gly Ala Glu Lys Ser Phe Gly Arg Asp Ile Val Asp Ala His Tyr
                165                 170                 175
Lys Ala Cys Leu Tyr Ala Gly Ile Asn Ile Ser Gly Ile Asn Gly Glu
            180                 185                 190
Val Met Pro Gly Gln Trp Glu Phe Gln Val Gly Pro Ser Val Gly Ile
        195                 200                 205
Ser Ser Gly Asp Gln Val Trp Val Ala Arg Tyr Ile Leu Glu Arg Ile
        210                 215                 220
Thr Glu Ile Ala Gly Val Val Thr Phe Asp Pro Lys Pro Ile Pro
225                 230                 235                 240
Gly Asp Trp Asn Gly Ala Gly Ala His Thr Asn Tyr Ser Thr Glu Ser
                245                 250                 255
Met Arg Lys Glu Gly Gly Tyr Glu Val Ile Lys Ala Ala Ile Glu Lys
            260                 265                 270
Leu Lys Leu Arg His Lys Glu His Ile Ala Ala Tyr Gly Glu Gly Asn
        275                 280                 285
Glu Arg Arg Leu Thr Gly Arg His Glu Thr Ala Asp Ile Asn Thr Phe
    290                 295                 300
Ser Trp Gly Val Ala Asn Arg Gly Ala Ser Val Arg Val Gly Arg Glu
305                 310                 315                 320
Thr Glu Gln Asn Gly Lys Gly Tyr Phe Glu Asp Arg Arg Pro Ala Ser
                325                 330                 335
Asn Met Asp Pro Tyr Val Val Thr Ser Met Ile Ala Glu Thr Thr Ile
            340                 345                 350
Val Trp Lys Pro
        355

<210> SEQ ID NO 9
<211> LENGTH: 36
<212> TYPE: RNA
<213> ORGANISM: Artificial
<220> FEATURE:
<223> OTHER INFORMATION: synthetic

<400> SEQUENCE: 9
cuccaaguga ccgagcaaga guuuuagagc uaugcu                                36

<210> SEQ ID NO 10
<211> LENGTH: 615
<212> TYPE: PRT
<213> ORGANISM: Zea mays

<400> SEQUENCE: 10

Met Ala Leu Ser Ala Ser Arg Val Gln Gln Ala Glu Glu Leu Leu Gln
1               5                   10                  15
Arg Pro Ala Glu Arg Gln Leu Met Arg Ser Gln Leu Ala Ala Ala Ala
            20                  25                  30
```

```
Arg Ser Ile Asn Trp Ser Tyr Ala Leu Phe Trp Ser Ile Ser Asp Thr
        35                  40                  45
Gln Pro Gly Val Leu Thr Trp Thr Asp Gly Phe Tyr Asn Gly Glu Val
 50                  55                  60
Lys Thr Arg Lys Ile Ser Asn Ser Val Glu Leu Thr Ser Asp His Leu
 65                  70                  75                  80
Val Met Gln Arg Ser Asp Gln Leu Arg Glu Leu Tyr Glu Ala Leu Leu
                 85                  90                  95
Ser Gly Glu Gly Asp Arg Arg Ala Ala Pro Ala Arg Pro Ala Gly Ser
                100                 105                 110
Leu Ser Pro Glu Asp Leu Gly Asp Thr Glu Trp Tyr Tyr Val Val Ser
                115                 120                 125
Met Thr Tyr Ala Phe Arg Pro Gly Gln Gly Leu Pro Gly Arg Ser Phe
130                 135                 140
Ala Ser Asp Glu His Val Trp Leu Cys Asn Ala His Leu Ala Gly Ser
145                 150                 155                 160
Lys Ala Phe Pro Arg Ala Leu Leu Ala Lys Ser Ala Ser Ile Gln Ser
                165                 170                 175
Ile Leu Cys Ile Pro Val Met Gly Gly Val Leu Glu Leu Gly Thr Thr
                180                 185                 190
Asp Thr Val Pro Glu Ala Pro Asp Leu Val Ser Arg Ala Thr Ala Ala
                195                 200                 205
Phe Trp Glu Pro Gln Cys Pro Thr Tyr Ser Glu Pro Ser Ser Ser
210                 215                 220
Pro Ser Gly Arg Ala Asn Glu Thr Gly Glu Ala Ala Asp Asp Gly
225                 230                 235                 240
Thr Phe Ala Phe Glu Glu Leu Asp His Asn Asn Gly Met Asp Ile Glu
                245                 250                 255
Ala Met Thr Ala Ala Gly Gly His Gly Gln Glu Glu Leu Arg Leu
                260                 265                 270
Arg Glu Ala Glu Ala Leu Ser Asp Asp Ala Ser Leu Glu His Ile Thr
                275                 280                 285
Lys Glu Ile Glu Glu Phe Tyr Ser Leu Cys Asp Glu Met Asp Leu Gln
290                 295                 300
Ala Leu Pro Leu Pro Leu Glu Asp Gly Trp Thr Val Asp Ala Ser Asn
305                 310                 315                 320
Phe Glu Val Pro Cys Ser Ser Pro Gln Pro Ala Pro Pro Val Asp
                325                 330                 335
Arg Ala Thr Ala Asn Val Ala Ala Asp Ala Ser Arg Ala Pro Val Tyr
                340                 345                 350
Gly Ser Arg Ala Thr Ser Phe Met Ala Trp Thr Arg Ser Ser Gln Gln
                355                 360                 365
Ser Ser Cys Ser Asp Asp Ala Ala Pro Ala Ala Val Val Pro Ala Ile
                370                 375                 380
Glu Glu Pro Gln Arg Leu Leu Lys Lys Val Val Ala Gly Gly Ala
385                 390                 395                 400
Trp Glu Ser Cys Gly Gly Ala Thr Gly Ala Ala Gln Glu Met Ser Gly
                405                 410                 415
Thr Gly Thr Lys Asn His Val Met Ser Glu Arg Lys Arg Arg Glu Lys
                420                 425                 430
Leu Asn Glu Met Phe Leu Val Leu Lys Ser Leu Leu Pro Ser Ile His
                435                 440                 445
Arg Val Asn Lys Ala Ser Ile Leu Ala Glu Thr Ile Ala Tyr Leu Lys
```

|  | 450 |  |  |  | 455 |  |  |  | 460 |  |  |  |
|---|---|---|---|---|---|---|---|---|---|---|---|---|
| Glu | Leu | Gln | Arg | Arg | Val | Gln | Glu | Leu | Glu | Ser | Ser | Arg | Glu | Pro | Ala |
| 465 |  |  |  |  | 470 |  |  |  | 475 |  |  |  | 480 |

Ser Arg Pro Ser Glu Thr Thr Thr Arg Leu Ile Thr Arg Pro Ser Arg
485 490 495

Gly Asn Asn Glu Ser Val Arg Lys Glu Val Cys Ala Gly Ser Lys Arg
500 505 510

Lys Ser Pro Glu Leu Gly Arg Asp Asp Val Glu Arg Pro Pro Val Leu
515 520 525

Ile Met Asp Ala Gly Thr Ser Asn Val Thr Val Thr Val Ser Asp Lys
530 535 540

Asp Val Leu Leu Glu Val Gln Cys Arg Trp Glu Glu Leu Leu Met Thr
545 550 555 560

Arg Val Phe Asp Ala Ile Lys Ser Leu His Leu Asp Val Leu Ser Val
565 570 575

Gln Ala Ser Ala Pro Asp Gly Phe Met Gly Leu Lys Ile Arg Ala Gln
580 585 590

Phe Ala Gly Ser Gly Ala Val Val Pro Trp Met Ile Ser Glu Ala Leu
595 600 605

Arg Lys Ala Ile Gly Lys Arg
610 615